United States Patent [19]

Cardon et al.

[11] 4,010,262

[45] Mar. 1, 1977

[54] METHOD FOR REDUCING THE INCIDENCE OF SCOURS IN MONOGASTRIC ANIMALS AND FOR THE TREATMENT OF SCOURS

[75] Inventors: Bartley P. Cardon; Howard M. Frederick, both of Tucson, Ariz.

[73] Assignee: Arizona Feeds, Tucson, Ariz.

[22] Filed: Oct. 6, 1975

[21] Appl. No.: 619,903

[52] U.S. Cl. .............................................. 424/180
[51] Int. Cl.² ....................................... A61K 31/715
[58] Field of Search ................................... 424/180

[56] References Cited

UNITED STATES PATENTS 3,911,114  10/1975  Cardon ............................. 424/180

Primary Examiner—Sam Rosen
Attorney, Agent, or Firm—Wills, Green & Mueth

[57] ABSTRACT

Monogastric animals such as pigs are fed a daily ration of pregelatinized starch in a paste form during the first 5 – 7 days after they are weaned.

9 Claims, No Drawings

METHOD FOR REDUCING THE INCIDENCE OF SCOURS IN MONOGASTRIC ANIMALS AND FOR THE TREATMENT OF SCOURS

BACKGROUND AND SUMMARY OF THE INVENTION

Newborn pigs usually remain with the sow for approximately twenty to thirty days, at which time each weighs approximately fifteen pounds.

The pigs are then taken from the sow, placed in community pens and fed a dry feed.

This weaning of the pigs and placing them in community pens causes the pigs to become stressed, and it is not unusual for 50% of them to have scours or diarrhea within two or three days after being placed in the pens.

Of the 50% which develop scours, it is not unusual for one fifth or 20% of the pigs with diarrhea to die, without treatment. Approximately 20% of the pigs with scours will recover without an appreciable loss of weight, but the other 60% of scoured pigs will lose a significant amount of weight through rapid dehydration, and this loss of weight must be made up through additional time and additional feed.

Obviously, there is a tremendous economic loss occasioned by the death of approximately ten percent of all weaned pigs, and a significant weight loss suffered by 30% of all weaned pigs.

Accordingly, it is an object of the present invention to provide a novel composition and method for reducing the incidence of scours in monogastric animals such as pigs, which is highly effective from the standpoint of almost completely preventing the occurrence of scours in newly weaned pigs.

Another object of the present invention is to provide a novel composition and method for treating weaned pigs which develop scours, whereby they can be quickly returned to normal and without an appreciable weight loss.

A further object of the present invention is to provide such a composition and method which is relatively inexpensive and easy to use.

We have discovered that the aforementioned objects and advantages are achieved by feeding to monogastric animals such as pigs, a daily ration of pregelatinized starch in a paste form, containing about 5 grams of pregelatinized starch.

DETAILED DESCRIPTION

For simplicity of explanation, the present invention is described as used with weaned pigs, but the invention is equally applicable for use with other newborn monogastric animals which are subject to stress which causes scours or diarrhea.

As mentioned above, pigs are weaned when they are about one month of age, at which time they are placed in community pens and fed a dry feed mix.

At the present time, 50% of the young pigs will develop scours within two or three days. Of the scoured pigs, some will recover without treatment and without an appreciable weight loss, whereas a significant number will die and an even greater number will lose significant amount of weight before recovering.

We have discovered that the incidence of scours in such newly weaned pigs can be greatly reduced, and in many instances practically eliminated, by feeding to the animal a daily ration of pregelatinized starch in an amount of approximately 5 grams, and preferably in a paste form.

The pregelatinized starch which we have used with considerable success was obtained from The Hubinger Company, Keokuk, Iowa, and sold by it under the designation "OK PRE-GEL". This is a pure, highly refined corn starch which is pregelatinized in water, dehydrated and pulverized to a white, finely granulated solid having a uniform particle size and a moisture content of about 3.5% to about 8.0%. The water absorption capacity of this pregelatinized starch is greater than 15 to 1.

We have successfully administered the pregelatinized starch to newly weaned pigs by mixing it with enough water to form a viscous paste, inserting a soft piece of rubber tubing past the trachea and into the esophagus of the animal, and then forcing the appropriate amount of pregelatinized starch paste through the tube. Tests were made to determine the effectiveness of the pregelatinized starch paste in reducing the incidence of scours in weaned pigs, and the treatment of scoured pigs using the same composition and method.

EXAMPLE I

A group of newly weaned feeder pigs, approximately 28 days of age and weighing between about thirteen and fifteen pounds each, were placed in steel cages and fed a 16% protein non-medicated pellet on a free choice basis. Water was also available on a free choice basis.

On the first day, each pig was assigned to one of the following groups:
 a. control: no pregelatinized starch,
 b. 1.0 grams of pregelatinized starch per day, and
 c. 5.0 grams of pregelatinized starch per day.

All pigs were observed for incidence of diarrhea, and scoured pigs were immediately removed from the trial.

Set forth below are the tabulated results:

|  | Grams of Pregelatinized Starch, Per Day | | |
| --- | --- | --- | --- |
|  | 0 | 1.0 | 5.0 |
| Number of pigs | 5 | 5 | 5 |
| Number with diarrhea | 5 | 2 | 0 |
| Time to onset of diarrhea, hours[1] | 36.0 | 48.0 | — |

[1]From the time pigs were placed in cages until diarrhea was observed.

As shown by the tabulated results, all control pigs were observed to have diarrhea after 36 hours on trial. Forty percent of the pigs given 1 gram of pregelatinized starch per day, scoured after 48 hours on trial, and 5 grams of pregelatinized starch per day completely prevented any scouring.

EXAMPLE II

A further trial was conducted to determine the efficacy of the pregelatinized starch to control and stop the diarrhea.

For this purpose, 20 newly weaned feeder pigs were separated out as soon as scouring was detected.

Eight of the pigs were classified as control, and remained on normal free choice food and water, without any special medication.

The remaining 12 pigs were each fed 5 grams of pregelatinized starch in paste form, once a day. The 12 treated pigs fully recovered with an average treatment of 2 days or 48 hours.

After the 8 control pigs remained untreated for 48 hours, each was fed 5 grams per day of pregelatinized starch in paste form, until fully recovered. The control pigs which did not receive the pregelatinized starch until after scouring for 48 hours, required an average of 3 days or 3 dosages before they fully recovered.

Thus, it has been clearly established that pregelatinized starch, fed to newly weaned pigs at a rate of about 5 grams per day, will drastically reduce the incidence of scours, and if scours occur, will cause the diarrhea to stop within a matter of a few days, and before there is any appreciable weight loss.

We claim:

1. The method of reducing the incidence of scours in monogastric animals, comprising feeding to the animal an effective amount of pregelatinized starch.

2. The method according to claim 1, in which the amount of pregelatinized starch is about five grams per day.

3. The method according to claim 1, in which the pregelatinized starch is mixed with water to form a viscous paste.

4. The method according to claim 1, in which the animal is a newly weaned pig and the feeding of the pregelatinized starch is started within two days after the pig is separated from its sow.

5. The method of claim 1, in which the pregelatinized starch is corn starch.

6. The method of treating stressed monogastric animals, comprising feeding the animal an effective amount of pregelatinized starch.

7. The method according to claim 6, in which the amount of pregelatinized starch is about five grams per day and the feeding is continued until the diarrhea is effectively stopped.

8. The method according to claim 6, in which the animal is a weaned pig.

9. The method according to claim 8, in which the pregelatinized starch has been mixed with water to form a viscous paste, and is fed to the animal through a tube which is inserted into the esophagus.

* * * * *

UNITED STATES PATENT AND TRADEMARK OFFICE
Certificate

Patent No. 4,010,262                                        Patented March 1, 1977

Bartley P. Cardon and Howard M. Frederick

Application having been made by Bartley P. Cardon and Howard M. Frederick, the inventors named in the patent above identified, and Arizona Feeds, Tucson, Arizona, a corportaion of Arizona, the assignee for the issuance of a certificate under the provisions of Title 35, Section 256, of the United States Code, deleting the name of Howard M. Frederick as a joint inventor, and a showing and proof of facts satisfying the requirements of the said section having been submitted, it is this 27th day of June 1978, certified that the name of the said Howard M. Frederick is hereby deleted from the said patent as a joint inventor with the said Bartley P. Cardon.

FRED W. SHERLING,
*Associate Solicitor.*